(12) United States Patent
Schmehl et al.

(10) Patent No.: US 6,779,521 B1
(45) Date of Patent: Aug. 24, 2004

(54) COMBINATION MOUTHPIECE FOR INHALATION THERAPY DEVICES USED BY OXYGEN DEPENDENT PATIENTS

(75) Inventors: Thomas Schmehl, Giessen (DE); Tobias Gessler, Wettenberg (DE); Werner Seeger, Biebertal (DE)

(73) Assignee: Medic-Aid Limited, Southhampton (GB)

(*) Notice: Subject to any disclaimer, the term of this patent is extended or adjusted under 35 U.S.C. 154(b) by 0 days.

(21) Appl. No.: 10/088,156

(22) PCT Filed: Sep. 14, 2000

(86) PCT No.: PCT/EP00/09112
§ 371 (c)(1),
(2), (4) Date: Jul. 23, 2002

(87) PCT Pub. No.: WO01/19436
PCT Pub. Date: Mar. 22, 2001

(30) Foreign Application Priority Data

Sep. 15, 1999 (DE) .......................................... 199 44 208
Sep. 15, 1999 (DE) .......................................... 299 16 220

(51) Int. Cl.⁷ ............................................. A61M 15/00
(52) U.S. Cl. ............................. 128/203.12; 128/200.18; 128/203.15; 128/203.233; 604/58
(58) Field of Search ..................... 128/200.18, 203.12, 128/203.15, 203.16, 203.22, 203.23, 204.11, 204.12, 205.11, 206.29, 202.27

(56) References Cited

U.S. PATENT DOCUMENTS 3,490,452 A * 1/1970 Greenfield ............. 128/200.23
4,790,305 A 12/1988 Zoltan et al.
4,926,852 A 5/1990 Zoltan et al.
5,413,095 A 5/1995 Weaver
5,497,765 A 3/1996 Praud et al.
5,701,886 A 12/1997 Ryatt
5,816,240 A 10/1998 Komesaroff
6,085,741 A 7/2000 Becker
6,390,090 B1 * 5/2002 Piper .................... 128/203.28

FOREIGN PATENT DOCUMENTS

| DE | 195 20 622 A1 | 12/1996 |
| DE | 197 55 600 A1 | 7/1999 |
| DE | 198 01 545 A1 | 8/1999 |
| DE | 299 08 080 U1 | 11/1999 |
| DE | 689 29 153 T2 | 6/2000 |
| EP | 0 855 224 A2 | 7/1998 |
| EP | 0 933 138 A2 | 8/1999 |
| EP | PCT/EP00/009112 | 9/2000 |
| GB | 2 333 236 A | 7/1999 |

* cited by examiner

*Primary Examiner*—Glenn K. Dawson
*Assistant Examiner*—Michael G. Mendoza
(74) *Attorney, Agent, or Firm*—Wiggin and Dana LLP; William A. Simons (57) ABSTRACT

A combination mouthpiece for inhalation therapy devices, having a body (1) defining an aerosol duct (2) through which, in use, a stream of air carrying an aerosolized drug is supplied to a patient during inspiration, an inlet hole (4) through the body for receiving in a releasable and secure manner an oxygen tube adapter (5), characterised by at least one partition (6) within the body (1) defining at least one oxygen duct (3), the oxygen duct being in a form such that it extends generally parallel with the aerosol duct (2) and has a flow cross-section sized in order to guide a suitably large oxygen stream from the oxygen tube adapter (5) through the inlet hole (4) to the patient.

17 Claims, 12 Drawing Sheets

COMBINATION MOUTHPIECE FOR INHALATION THERAPY DEVICES USED BY OXYGEN DEPENDENT PATIENTS

The present invention relates to a mouthpiece for inhalation therapy devices used by oxygen dependent patients.

The delivery of medicines to patients by inhalation therapy is an important treatment for many illnesses. Some patients who benefit from such a therapy require a constant supply of oxygen in order to maintain a sufficient level of oxygen in their blood. For various reasons, devices for delivering medicines for inhalation therapy use air to carry the medicine in the patient's respiratory air flow. Thus, such therapy interrupts the supply of oxygen to the patient which can lead to negative clinical symptoms such as dizziness, tightness and fainting, due to the decrease oxygen level in the blood. Inhalation therapy typically lasts as long as twenty minutes, and interruption of the oxygen supply for that long will result in a rapid decrease in the level of oxygen in the blood for such patients. Patients who typically require high levels of oxygen in their inspiratory air flow include those suffering from pulmonary hypertension and COPD. It is clinically important to maintain the correct levels of oxygen in the blood of such patients, and also to deliver the appropriate drugs effectively and quickly.

Figure 1:
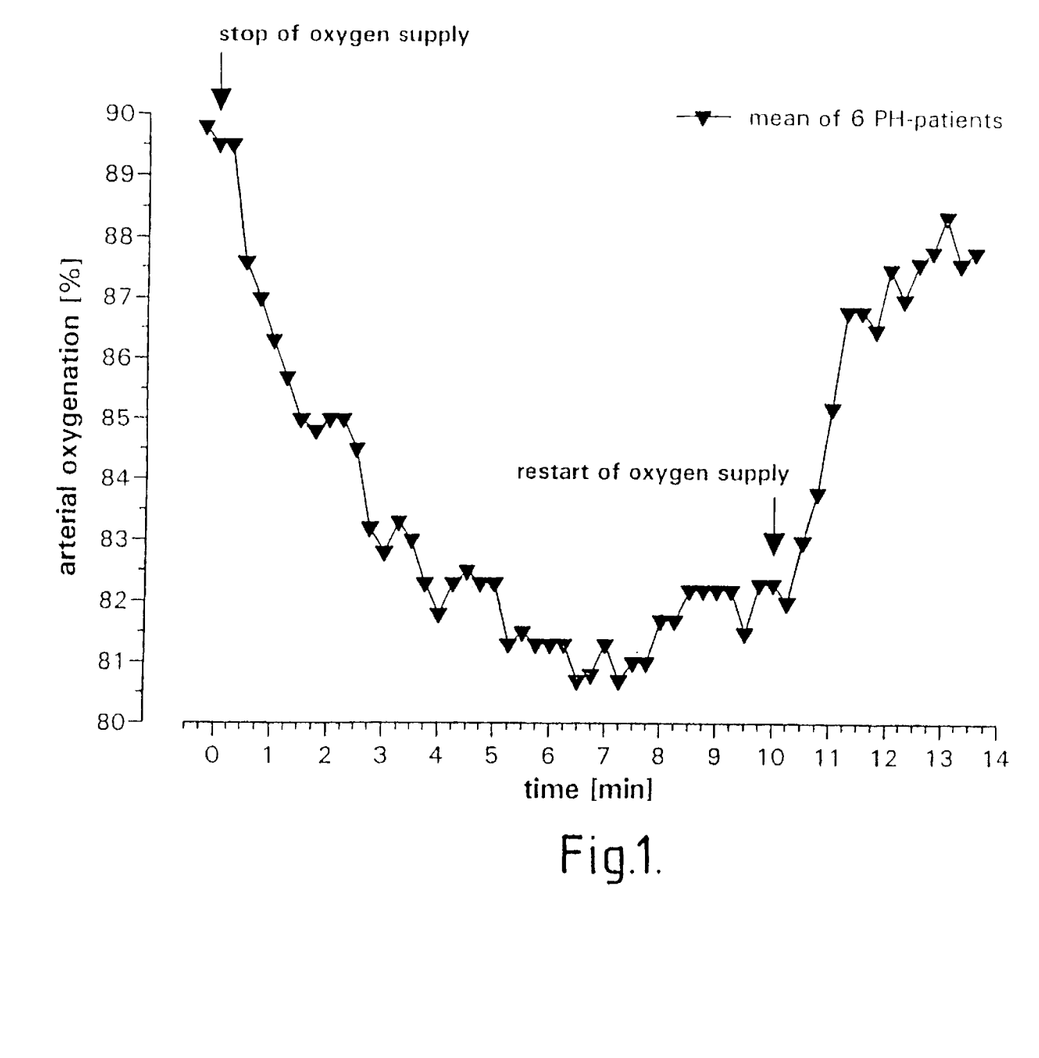

To fully appreciate the effect of interrupting the oxygen supply to pulmonary hypertension patients, graphs are shown in FIGS. 1 to 6 which show the drop in arterial oxygenation. In FIG. 1, a graph shows an initial arterial oxygenation level of nearly 90% at the time of interrupting the oxygen supply to the patient. From that time, the patient is breathing air instead of oxygen. As will be seen, the level of oxygenation drops extremely to just over 80%. On restarting the supply of oxygen to the patient, the arterial oxygenation level increases quite quickly to a level of about 87% before beginning a more gradual ascent towards the oxygenation level present before treatment started.

Figure 2:
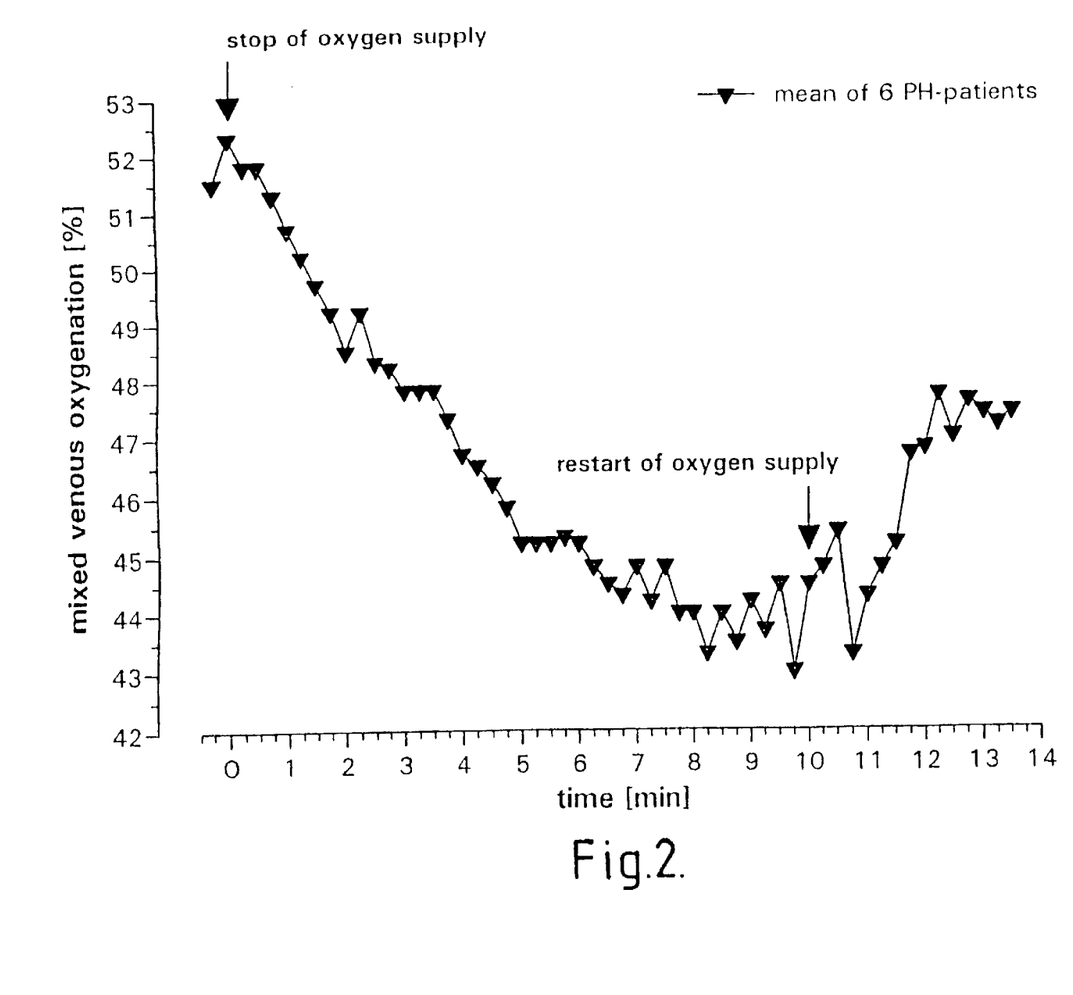

FIG. 2 is a graph showing the mixed venous oxygenation of a patient during the same experiment as is shown in FIG. 1. The oxygenation starts at about 52% when the oxygen supply is interrupted and replaced with air. The oxygenation level drops steadily during the ten minutes of the oxygen interruption to about 44%. Once oxygen supply to the patient is restarted, the oxygenation level increases only gradually.

Figure 3:
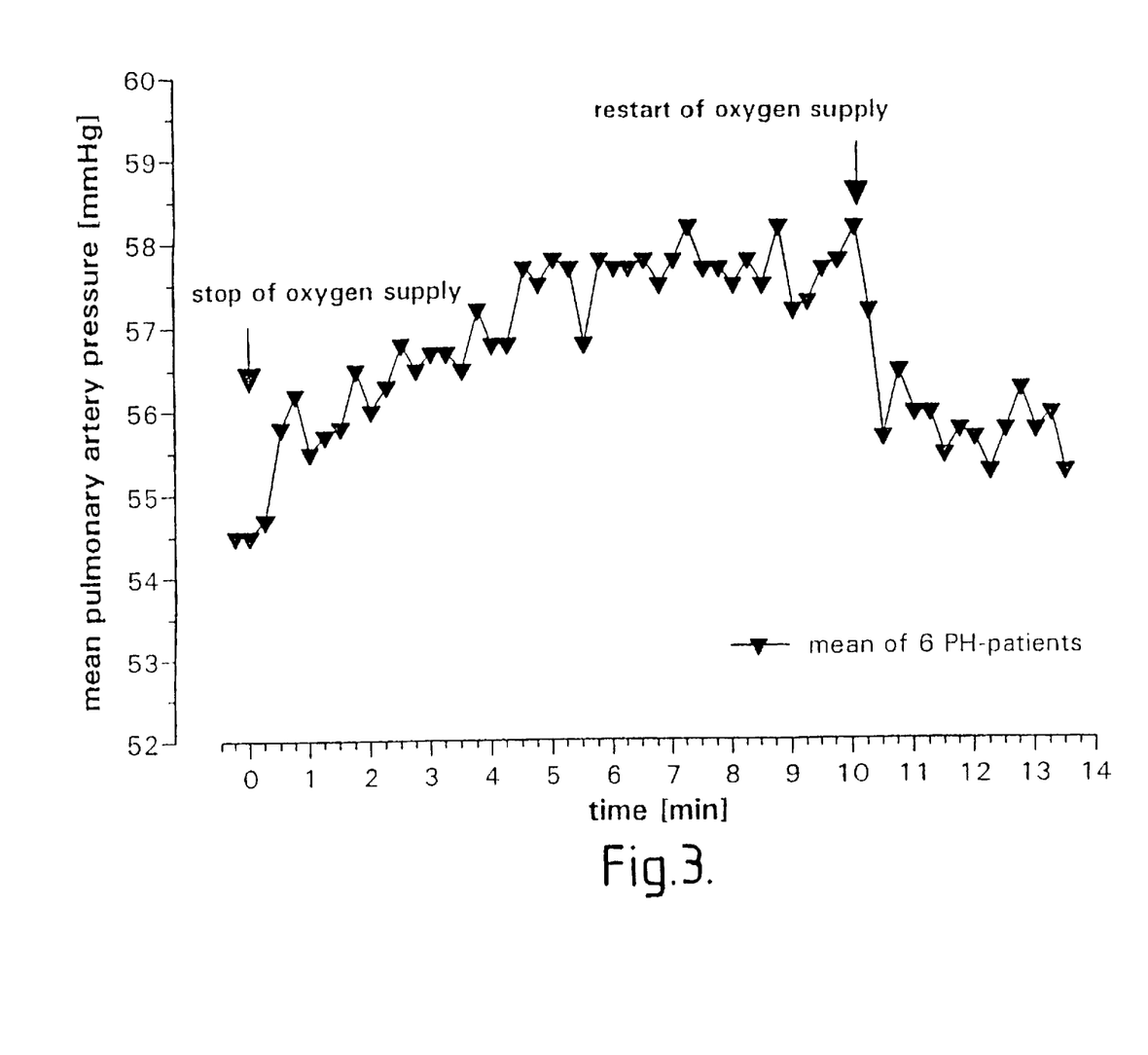

In order to indicate just how serious this reduction in oxygenation of the blood has on the patient, the FIG. 3 shows a graph of the mean pulmonary artery pressure over the period of the experiment shown in FIGS. 1 and 2. As will be seen, as soon as the oxygen supply is withdrawn from the patient and replaced with an air supply, the pressure increases from about 54.5 mmHg to about 58 mmHg. In the patients suffering from ailments such as pulmonary hypertension and COPD, such an increase is clinically extremely undesirable and can make the symptoms worse.

It is, therefore, desirable to deliver a sufficient level of oxygen in the respiratory air flow of a patient while at the same time delivering a drug into the air stream of a patient for inhalation.

DE 19755600 A1 and EP 0855224 A2 disclose jet nebulizers which use compressed air supplied by a compressor or compressed air cylinder, to produce an aerolized medicine. If operating in conjunction with a compressed air cylinder, it is possible to use compressed oxygen instead of air. This allows the inhalation gas to be partially enriched with oxygen. However, the compressed gas which causes atomization contributes only a small part of the gas stream leading to the patient during inhalation. However, this also necessitates an appropriate oxygen pressure pipe or a compressed oxygen canister with a pressure-reducing valve mechanism which is usually only available in a few hospitals, medical practices or clinics. In fewer patients who have the necessary equipment at home, the ability to treat patients at home is important to maintain patients' standard of living and to maintain treatment at lower cost.

In theory, this problem could be solved by inhalation inside an oxygen tent. The gas entering the nebulizer would then be oxygen, and the patient would then receive the required level of oxygen. However, the application of this solution is considerably limited by the unwieldy nature of such a tent. It should be appreciated here that the vast majority of gas inhaled by a patient using such a nebulizer is ambient air drawn into the device during inhalation.

EP 0933138 discloses ultrasonic nebulizers which use an ultrasonic field to atomize the medicine, the medicine then being carried in aerosol form in a stream of air being inhaled by the patient. Most require an external gas flow to discharge the produced aerosol. The oxygen tent could again be used to enrich the aerosol inhaled with oxygen, but with the resultant disadvantages. Another possibility would be to introduce an appropriate volume of oxygen into the ultrasonic chamber, but this would entail a continuous aerosol discharged both during inhalation and exhalation which substantially reduces the efficiency of the aerosolizing process. Much drug, may be as much as 80% to 90% would then be wasted.

DE 19801545 discloses how advancement in mouthpiece design do not address the possibility of providing continuous oxygenation during inhalation.

According to the present invention, a combination mouthpiece for inhalation therapy devices, is arranged to supply both a stream of air carrying an aerosolized drug and oxygen, and has a body defining an aerosol duct through which, in use, the stream of air carrying the aerosolized drug is supplied to a patient during inspiration, an inlet hole through the body for receiving in a releasable and secure manner an oxygen tube adapter, characterised by at least one partition within the body defining at least one oxygen duct, the oxygen duct being in a form such that it extends generally parallel with the aerosol duct and has a flow cross-section sized in order to guide a suitably large oxygen stream from the oxygen tube adapter through the inlet hole to the patient. In this way oxygen dependent patients can receive inhaled therapy treatment and oxygen rich gas for inhalation so as to maintain the oxygen levels in the blood while still delivering the appropriate drug.

Further aspects of the invention, as well as preferred features of the present invention are referred to in the claims.

Embodiments of the present invention will be described below by reference to the accompanying drawings in which:

FIG. 1 is a graph showing the drop in arterial oxygenation after the interruption of oxygen supplied to a patient over time;

FIG. 2 is a graph showing a drop in mixed venous oxygenation over time following the interruption of oxygen to a patient;

FIG. 3 is a graph showing the increase in mean pulmonary artery pressure over time following the interruption in oxygen supply to a patient;

FIG. 4 is a graph showing the arterial oxygenation level over time as a result of three different treatments;

FIG. 5 is a graph showing the mixed venous oxygenation level over time during three different treatments;

FIG. 6 is a graph showing the mean pulmonary artery pressure over time during three different treatments;

Figure 7:
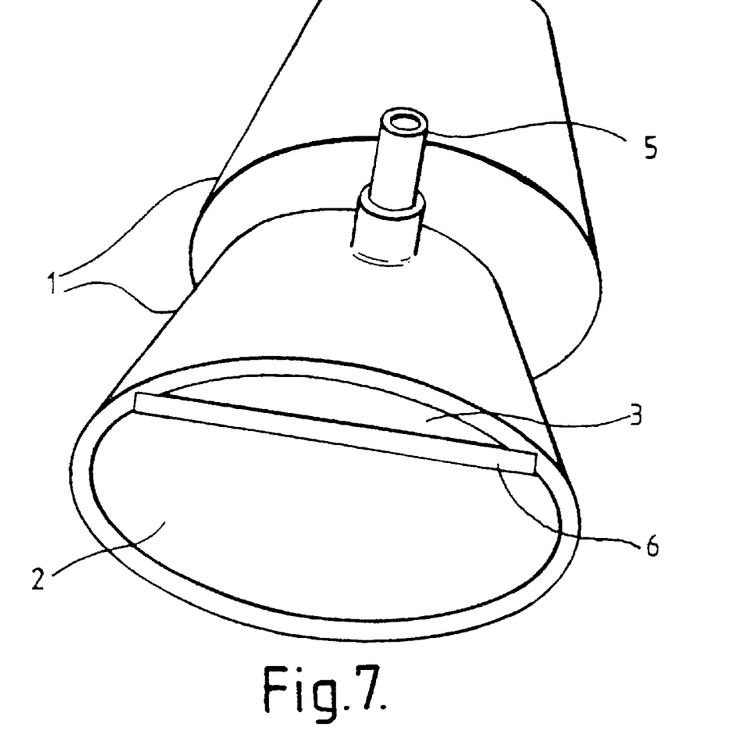
FIG. 7 is a perspective view of a mouthpiece according to the present invention.
Figure 8:
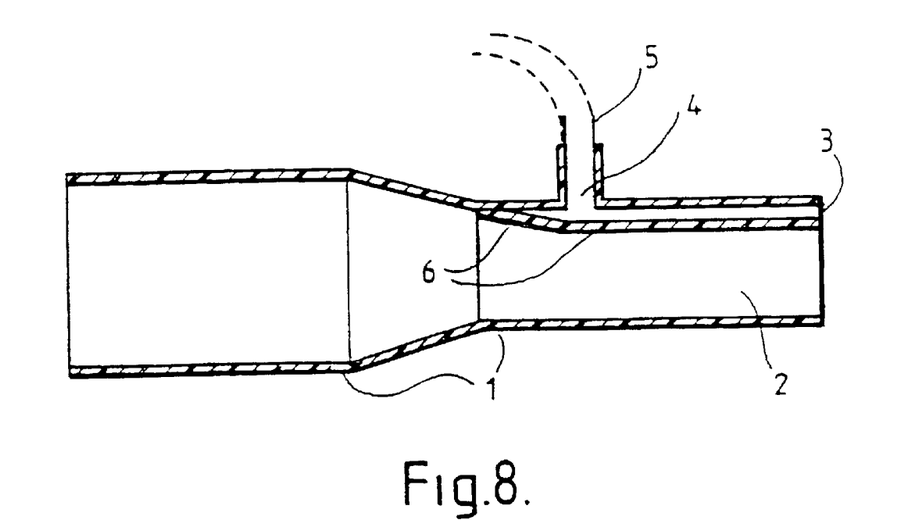
FIG. 8 is a cross-sectional view of the mouthpiece shown in FIG. 7.

Referring first to FIGS. 7 and 8, a mouthpiece is shown having a generally tubular body 1 which extends from a first end which forms the mouth end opening 2 of the mouthpiece to the opposite end which is nearer the source of aerosolized medicine during use. The tubular body 1 also includes an inlet hole 4, which may be a drilled hole, in which is located a hose adaptor 5 by which a hose may be attached to supply oxygen via the hole 4 into the mouthpiece. A partition 6 is located within the mouthpiece which defines an oxygen duct 3. This duct is arranged along the mouthpiece to lead oxygen entering the mouthpiece via the hole 4 to the mouth end opening of the mouthpiece. The oxygen channel 3 is arranged to prevent the entry of air from the rest of the mouthpiece which constitutes the aerosol duct 2. A connecting post 7 (not shown) is included to support the partition and to allow adjustment of the rate of flow of oxygen through the oxygen duct. This feature is described in more detail in the later embodiment.

In this embodiment, the partition ends flush with the end of the tubular body 1 at the mouth end opening of the mouthpiece. This avoids unwanted interaction between the aerosol and the oxygen flow. It also ensures that operation of commercial nebulizers such as breath-activated devices is not impaired. Aerosol production and the flow of aerosolized air within the nebulizer and the inhalation process are not impaired in any way by using the mouthpiece.

It will be appreciated that this mouthpiece can be used on various different types of atomizer. Later in this description, the use of this atomizer together with a jet-type atomizer will be described, although it is not limited to that type of atomizer. What is important is being able to deliver a medicine in aerosol form to patient whilst delivering oxygen-rich air to the patient to maintain oxygen levels in the blood. This is achieved by the continuous supply of oxygen by the oxygen duct 3, so that when the patient breathes, the majority of the gas inhaled by the patient will be oxygen. To that will be added a flow of aerosol-laden air via the aerosol duct 2. As the patient inhales, aerosolized air is inhaled by the patient together with the oxygen. Probably in the region of 20% of the volume of gas which patient inhales is oxygen. During exhalation, the exhaled air from the patient passes down the aerosol duct to the atomizer where it is exhausted to atmosphere. The atomizer, as will be described later, will normally only deliver the aerosol during inhalation and not during exhalation in order to avoid wastage of the drug.

Figure 9:
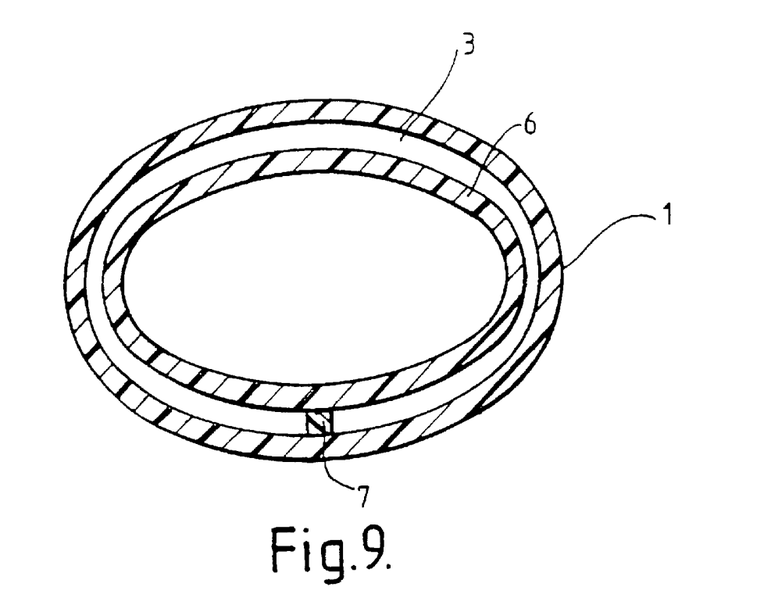
FIG. 9 is a vertical cross-sectional view of a second mouthpiece according to the invention.
Figure 10:
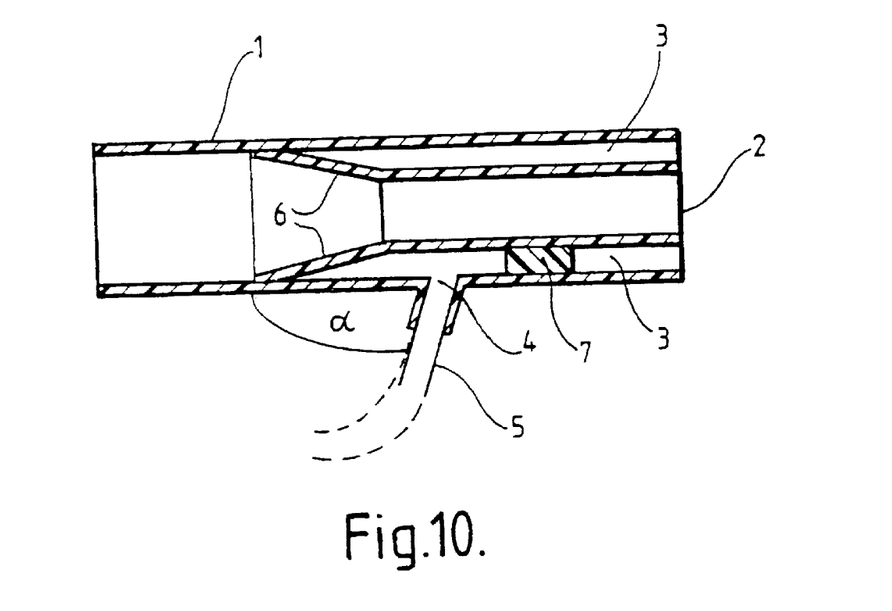
FIG. 10 is a transfer-sectional view through the mouthpiece of FIG. 9.

Referring now to FIGS. 9 and 10, a second embodiment of the mouthpiece is shown in which the oxygen duct 2 is generally annular, and surrounds the aerosol duct 2. The partition 6 is tubular in order to form the generally annular oxygen duct 3, and extends from just upstream of the inlet hole 4 where it tapers inwardly from the inner wall of the tubular body 1 in order to close the oxygen duct 3 from the flow of aerosol air passing through the mouthpiece to the mouth end opening of the mouthpiece. The partition finishes flush with the mouth end of opening of the mouthpiece. Thus, in use, during inhalation, the medication-laden air passing through the aerosol duct 2 enters the patient's mouth surrounded by oxygen from the oxygen duct 3. The mouthpiece also includes a connecting post or web 7 which is located between the partition 6 and the tubular body 1 in order to support the partition. It also offers flow resistance immediately downstream of the inlet hole to ensure an even distribution of oxygen around the annular oxygen duct 3.

Figure 11:
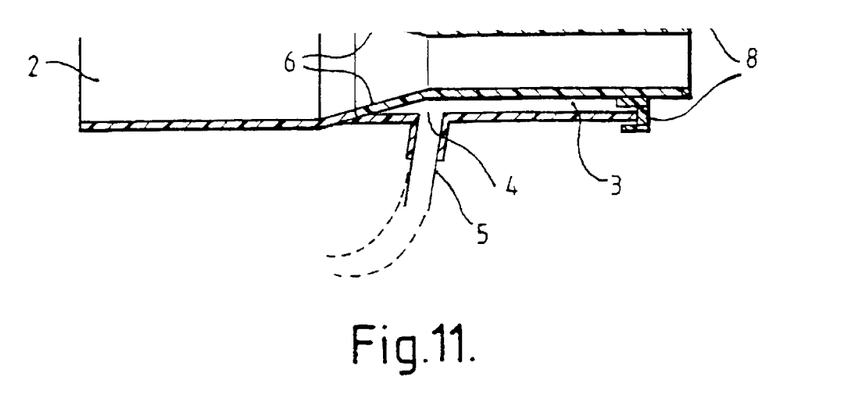
FIG. 11 is a longitudinal sectional view of a further mouthpiece according to the present invention.

Referring now to FIG. 11, a similar mouthpiece is shown to that of FIG. 10. However, the oxygen channel does not end flush with the mouth end opening of the aerosol channel. In fact, the partition 6 extends beyond the end of the tubular body 1. Such an arrangement may be advantageous in certain circumstances. In addition, a closure or stopper 8 is shown which may be locked in place at the downstream end of the oxygen duct in order to prevent the supply of oxygen to the patient, where the patient does not require an oxygen-rich gas for inhalation. A pad (not shown) can be attached to the end of the oxygen channel or to the outside of the tubular body 1 in order to allow the patient to rest his teeth behind. This assists with the correct location of the mouthpiece with respect to the patient's mouth.

Figure 12:
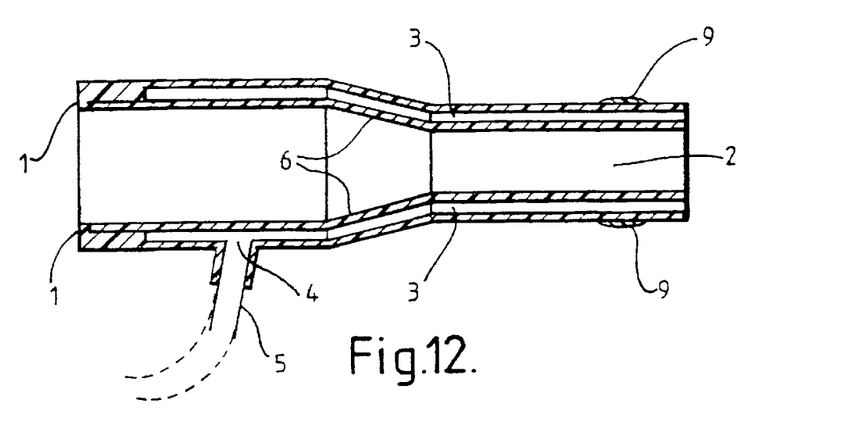
FIG. 12 is a longitudinal sectional view of a fourth embodiment of the present invention.

Referring now to FIG. 12, a fourth embodiment of the mouthpiece is shown in which the oxygen channel is formed as an extension of the wall of the body 1. In this way, the oxygen hose adaptor 5 can be attached further away from the mouth opening which reduces the chance of prominent facial features such as the nose and chin interfering with the oxygen hose adaptor and also increases comfort. Thus, the partition is longer than in the previous embodiments. A pad 9 is shown on the tubular body 1 near the mouth end opening of the mouthpiece. This pad is placed on the outside of the mouthpiece for the comfort of the user's lips and teeth, and typically lies a maximum of 1 cm from the mouth end opening of the body 1. Depending on the shape of the pad, the patient may wish to rest his lips or his teeth on or behind the pad. This pad assists with the location of the mouthpiece with respect to the patient's mouth.

Figure 13:
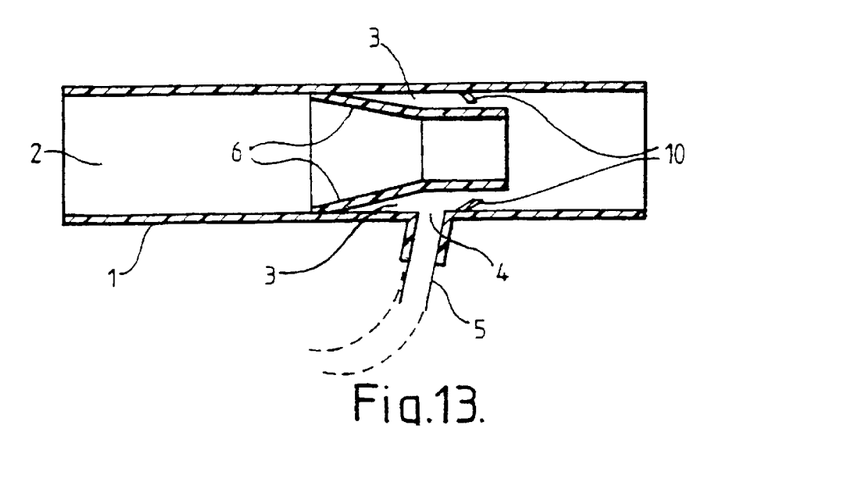
FIG. 13 is a longitudinal sectional view of a fifth embodiment of the present invention.

Referring now to the fifth embodiment shown in FIG. 13, the partition 6 does not end flush with the mouth end opening of the tubular body 1, but at some distance from it within the body. The appropriate distance between the end of the partition 6 and the end of the tubular body 1 depends on the size of the annular oxygen duct. Within the oxygen duct, shortly before the end of the partition 6, a circular flow aperture 10 is located in the form of a ring attached to the inside of the tubular body 1 and directed generally inwardly of the body and forwarding the direction of flow of oxygen. This constricts the flow of oxygen through the oxygen duct, and if correctly designed creates an extensive homogenous and laminar oxygen flow from the end of the oxygen duct up to the mouth end opening of the tubular body. The length of the partition, the diameter of the circular flow aperture and the width of the annular gap should be calculated so that they operate correctly with each other to have the optimum effect.

Figure 14:
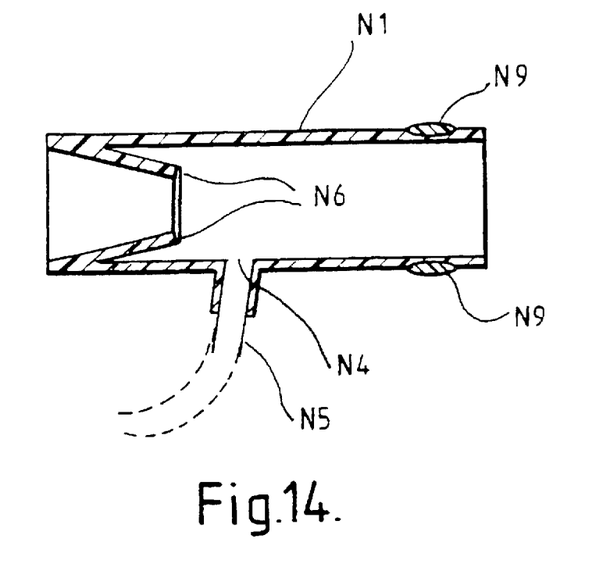
FIG. 14 is longitudinal sectional view of a sixth embodiment of the present invention.
Figure 15:
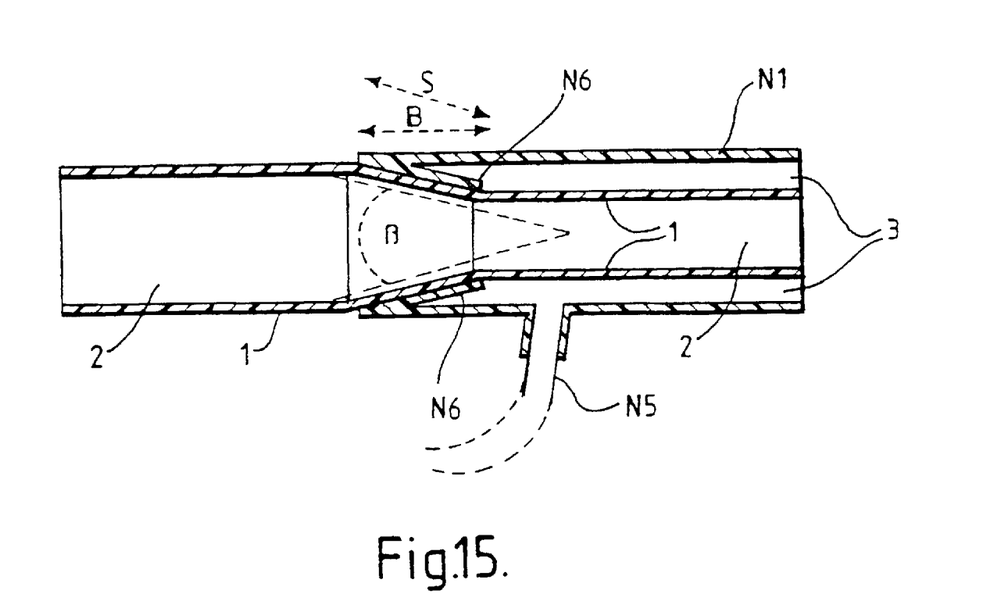
FIG. 15 is a longitudinal sectional view of a further embodiment of the present invention.

Referring now to FIG. 14, a cross-sectional view of a supplementary part N is shown for addition to a mouthpiece which does not include an oxygen duct. The supplementary part N is shown fitted to such a mouthpiece in FIG. 15. The supplementary part N includes a tubular body N1, an oxygen hose adapter N5, an inlet hole N4 and a funnel-shaped ring N6. It is designed to fit on a commonly available mouthpiece as is shown in FIG. 15. Once fitted, the tubular body N1 forms the outside of the tubular body 1, the commonly available mouthpiece forms the partition labeled 1 and they are attached together along the funnel-shaped ring N6 which is angled to correspond with a taper on the commonly available mouthpiece. Of course, the shape and configuration of the supplementary part N will depend entirely on the mouthpiece to which it is to be fitted. The tapering body in this case has an opening angle of β, the same as the angle of the taper on the mouthpiece to which the supplementary part has been added. The opening angle β and the width B of the funnel-shaped ring N6 are adapted to the taper angle β or to the tapering position S of the body 1 in such a manner that the retrofit kit is in a form such that it can be slipped over the body 1 with a spacing of at least one millimeter therefrom. Of course, any of the features of the five embodiments described above can be included in this supplementary part. Thus, retro-fitting of this invention is possible.

An annual bead N9 is fitted to the outside to the tubular hollow body N1. Also, the funnel shaped ring N6 can be secured to the body firmly, for example by adhesive bonding.

Figure 16:
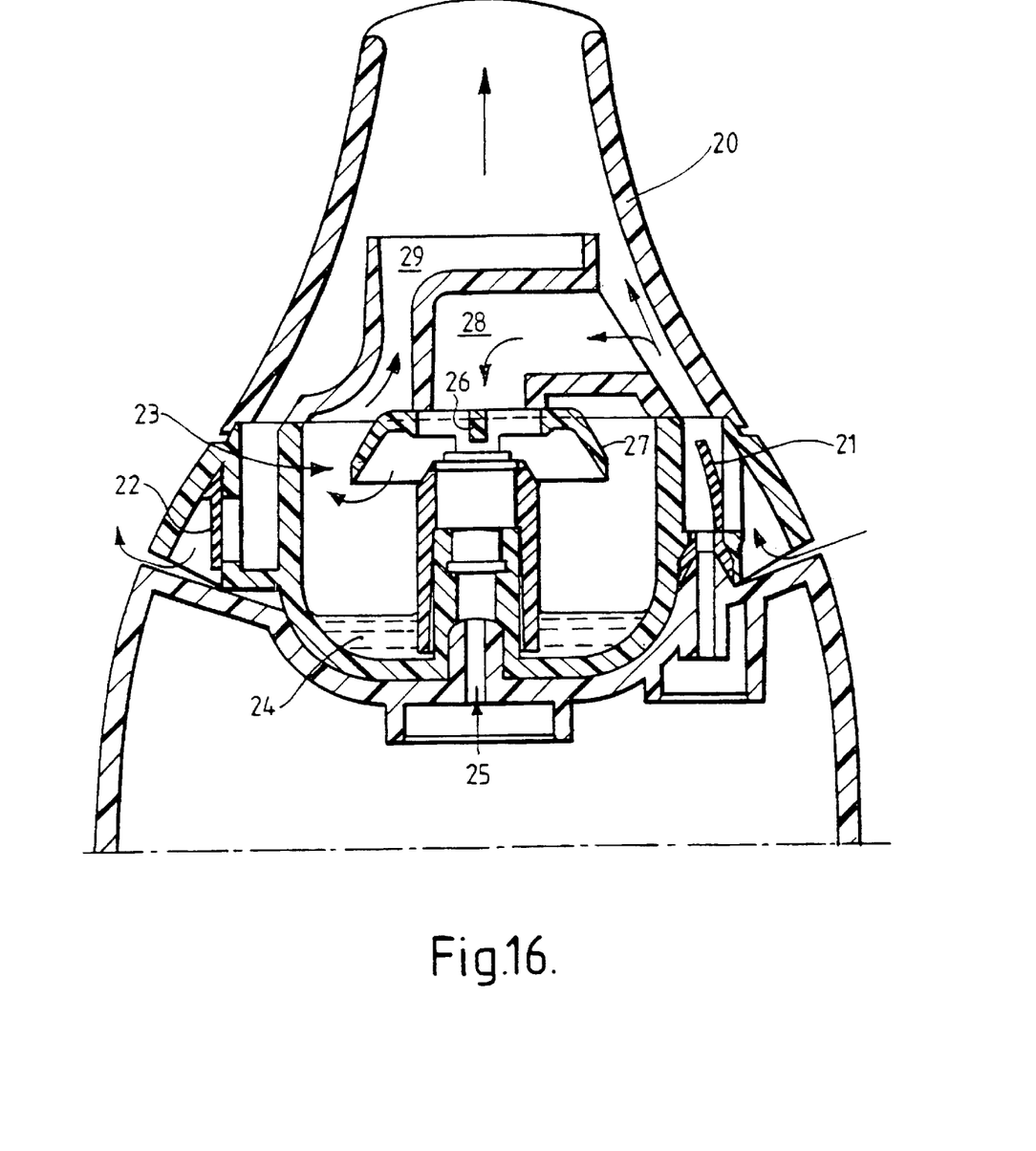
FIG. 16 is a sectional view of an atomizer having a mouthpiece according to the present invention.
Figure 17:
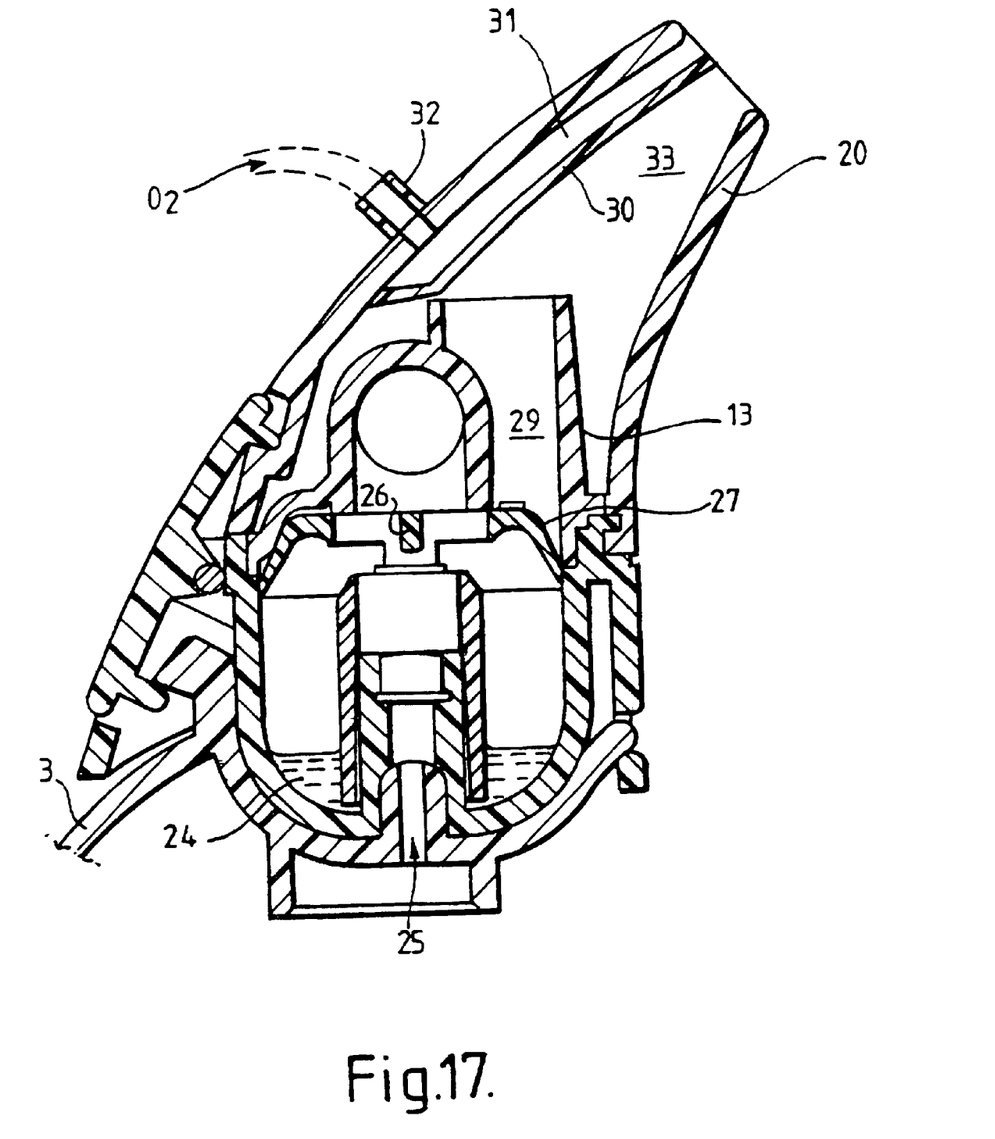
FIG. 17 is another sectional view of the atomizer shown in FIG. 16.

Referring now to FIGS. 16 and 17, an atomizer is shown to which this invention has been applied. The atomizer concerned is the subject of International patent application number WO97/48431, the contents of which are hereby embodied. The atomizer shown is based on a commercially known atomizer made by Medic-Aid Limited and sold under the trade mark HaloLite (registered trade mark). Therefore, the operation of the atomizer will not be described in great detail below.

The atomizer includes a mouthpiece 20 which is mounted on the top of the device and through which a patient breathes, both inhaling and exhaling. During inhalation, a flap valve 21 opens to allow ambient air to enter the atomizer and during exhalation, another flap valve 22 opens in order to allow the exhaled air to escape to the surroundings. In the centre of the atomizer is an atomizing unit 23 for atomizing a medicine 24 in liquid or suspension form located within a reservoir. Atomization is driven by a flow of gas, normally air, but possibly oxygen 25 which is directed from a pressure source (not shown) to a jet outlet located immediately beneath a deflector bar 26. The deflector bar 26 deflects the stream of gas transversely, and this generates a low pressure region on either side of the jet outlet. The medicine 24 is drawn upwardly by this low pressure and atomized in the region below and to either side of the deflector bar 26. Air passes through a first passageway 28 and entrains the atomized medicine and carries it down beneath the mushroomed-shaped baffle 27 and back up through a second passageway 29. Any droplets of the medicine which are too large will collide with the inside of the mushroom-shaped baffle 27, coalesce on its underside and dropped back into the reservoir. In the HaloLite product, atomization only occurs during inhalation. A pressure sensor (not shown) detects when a patient begins to inhale in order to trigger a pulse of pressurized gas 25 to start atomization. Thus, the wastage of the product is reduced. Clearly, during exhalation, it is not desirable to atomize the drug since some of these will be lost to the atmosphere as the exhaled air passes through flap valve 22. In FIG. 16, since it is a sectional view, the present invention is not visible. However, in the side sectional view of FIG. 17, it will be seen that the mouthpiece 20 includes a partition 30 opening at the mouth end opening of the body of the mouthpiece of the nebulizer. The partition defines an oxygen duct for supplying oxygen to the patient from a hose adaptor 32 adjacent a hole through the outer wall of the mouthpiece. An oxygen supply pipe can be attached to the hose adaptor 32 for supplying oxygen to the oxygen duct.

On the other side of the partition 30 is an aerosol duct 33 for supplying aerosolized medicine from the atomizing unit 23.

In use, the patient inhales and exhales through the mouthpiece, and during inhalation, is supplied with oxygen from the oxygen source via the hose adaptor 32, the hole in the mouthpiece, and the oxygen duct 31. The oxygen is supplied via a regulator and flow meter which effectively allows oxygen to be supplied at ambient pressure. The supply source prior to the regulation will typically be at a few atmospheres. Also, during inhalation, the pressure within the atomizer will drop triggering atomization to occur by pressurized gas 25 being directed from a jet outlet onto the deflector 26 which will draw the medicine 24 up from the reservoir and atomize it. The inhaled airstream enters the atomizer via flap valve 21, and part of that inhaled airstream passes through the first passageway 28 into the region of atomization of the atomizing unit to entrain the medicine before being deflected beneath the mushroom-shaped baffle and back up through the second passageway 29 laden with air. The air-laden with aerosol medication then passes up through the aerosol duct 33 to the patient.

During exhalation, inhaled air passes down through the aerosol duct, and since an increase pressure will be detected within the atomizer, atomization will be switched off. The exhaled air will then be vented to atmosphere via the flap valve 22.

Clinical tests have recently been carried out in order to discover the effectiveness of this invention. In a first test, six oxygen dependent patients with severe pulmonary hypertension and a mean oxygen nasal flow of 5 liters per minute were selected, and all patients inhaled Iloprost (which is a trade mark), a stable prostocyclin analogue made by Schering.

The patients were investigated under right heart catheterization at the intensive care unit. Arterial and mixed venous oxygenation were continuously monitored. Before starting the inhalation manoeuvres oxygen supply was stopped for a period of ten minutes to assess the drop of oxygen saturation. The results of this test are shown in FIGS. 1 to 3. After this base line measurement, three different inhalation manoeuvres of approximately ten minutes duration were performed using a HaloLite (registered trade mark) jet nebulizer in randomized order and two hour wash out period between the inhalations:

1. Inhalation of 2.5 μg Iloprost without additional oxygen;
2. Inhalation of 2.5 μg Iloprost without additional oxygen the proposed oxygen mouthpiece;
3. Inhalation of 2.5 μg Iloprost without additional oxygen administered by nasal tube.

Pre- and post-interventions the patients were supplied with their habitual oxygen flow via a nasal tube. This oxygen flow rate was maintained during interventions 2 and 3 above.

The results of this test were as follows:

The withdrawal of oxygen decreased arterial oxygenation from 89.8±1.9% to 8.0±3.1% and mixed veinous oxygenation from 51.5±3.3% to 43.0±4.0%. The restart of oxygen supply lead to restoration of the arterial and mixed veinous oxygenation to base line values.

Inhalation of the radioactive Iloprost without oxygen reduced arterial saturation from 88.8±3.2% to 83.5±2.9%, whereas inhalation of oxygen via the mouthpiece increased arterial saturation from 89.3±2.7% to 92.8±1.4%. Inhalation with nasal oxygen slightly decreased arterial saturation from 89.5±2.8% to 87.3±2.6%. Due to the hemodynamic effects of Iloprost, the mixed veinous saturation was increased from 49.0±3.7% to 51.2±4.2% (1) from 49.7±2.7% to 58.5±3.1%, (2) and from 47.8±4.2% to 54.3±3.9% (3).

The investigation demonstrates that the blood oxygen saturation of the oxygen-dependent pulmonary hypertension patients decreases dramatically, even if the oxygen supply is stopped only for a short period of ten minutes. The inhalation with maintenance of the oxygen supply by the prosposed mouthpiece was superior to the other modes of inhalation. Contrary to the inhalation without oxygen and oxygen through a nose tubing, the arterial saturation increased during inhalation with the mouthpiece. The mixed venous saturation also improved best with the most prominent clinical benefit by the use of the proposed mouthpiece.

In a second test, a different drug, a bronchodilator was used.

Patients

Two oxygen-dependent patients with chronic obstructive pulmonary disease and a mean oxygen nasal flow of 2.3 L/min. All patients inhaled the bronchodilator fenoterol.

Protocol

Arterial oxygenation was continuously monitored by transcutaneous oxymetry. Three different inhalation maneuvers of approximately ten minutes duration were performed with a Halo-lite™ jet nebulizer in randomized order:

i) Inhalation of fenoterol without additional oxygen.

ii) Inhalation of fenoterol with additional oxygen administered via the proposed oxygen mouthpiece.

iii) Inhalation of fenoterol with additional oxygen administered via nasal tube.

Pre and post interventions the patients were supplied with their habitual oxygen flow via a nasal tube. This oxygen flow rate was maintained during interventions ii) and iii).

Results

Inhalation of fenoterol without oxygen reduced arterial saturation from 96.5% to 92.5%, whereas inhalation with oxygen via the mouthpiece increased arterial saturation from 96.5% to 98.5%. Inhalation with nasal oxygen decreased arterial saturation from to 97.5% to 94.0%. One patient had to stop inhalation without oxygen after five minutes because of severe dyspnea.

The inhalation with oxygen supply by the prosposed mouthpiece improved arterial oxygenation, whereas both other modes resulted in a decrease of oxygen saturation. Such drop in oxygenation and the resulting dyspnea may lead to interruption of inhalation therapy, as demonstrated in one patient. Other bronchodilators besides Fenoterol can be used for COPD patients, such as Salbutamol, and Salmeterol.

Figure 4:
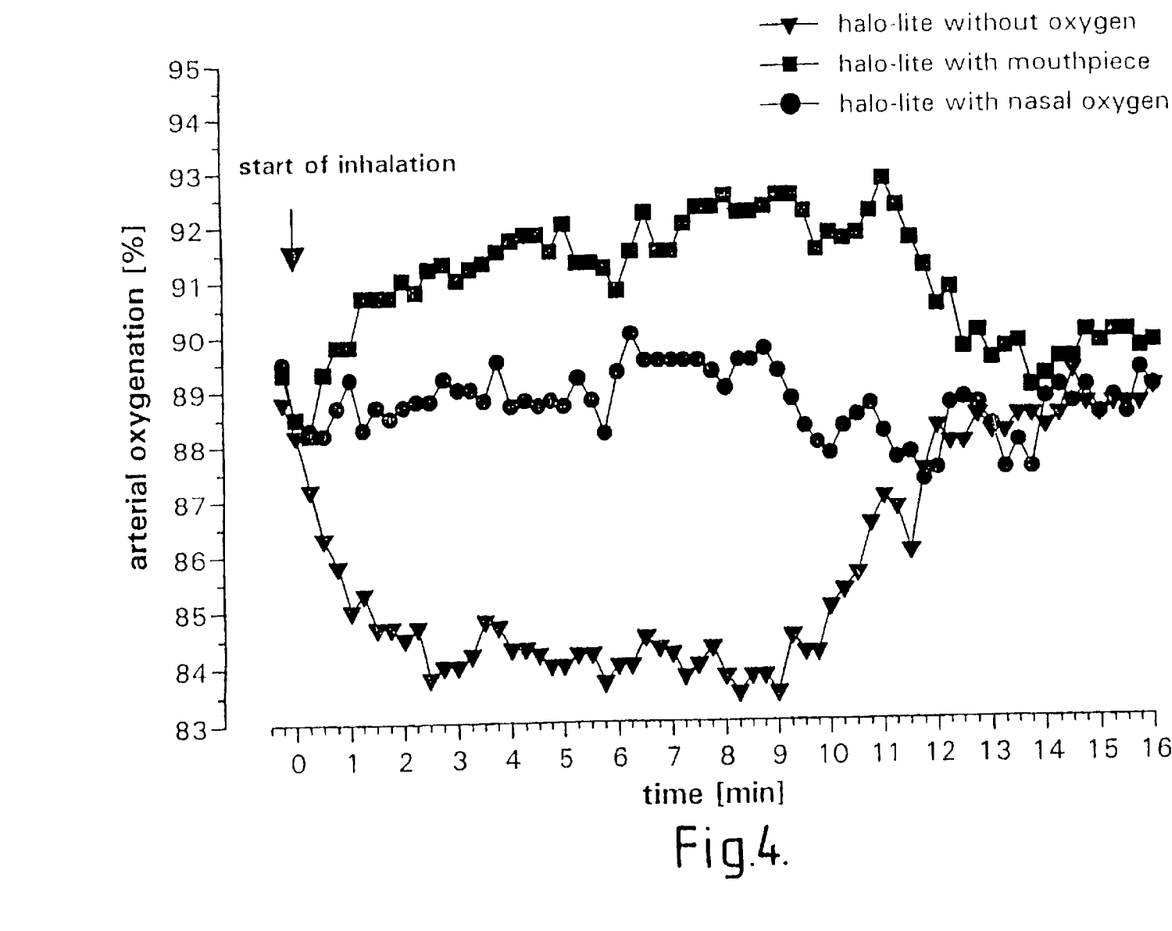
Figure 5:
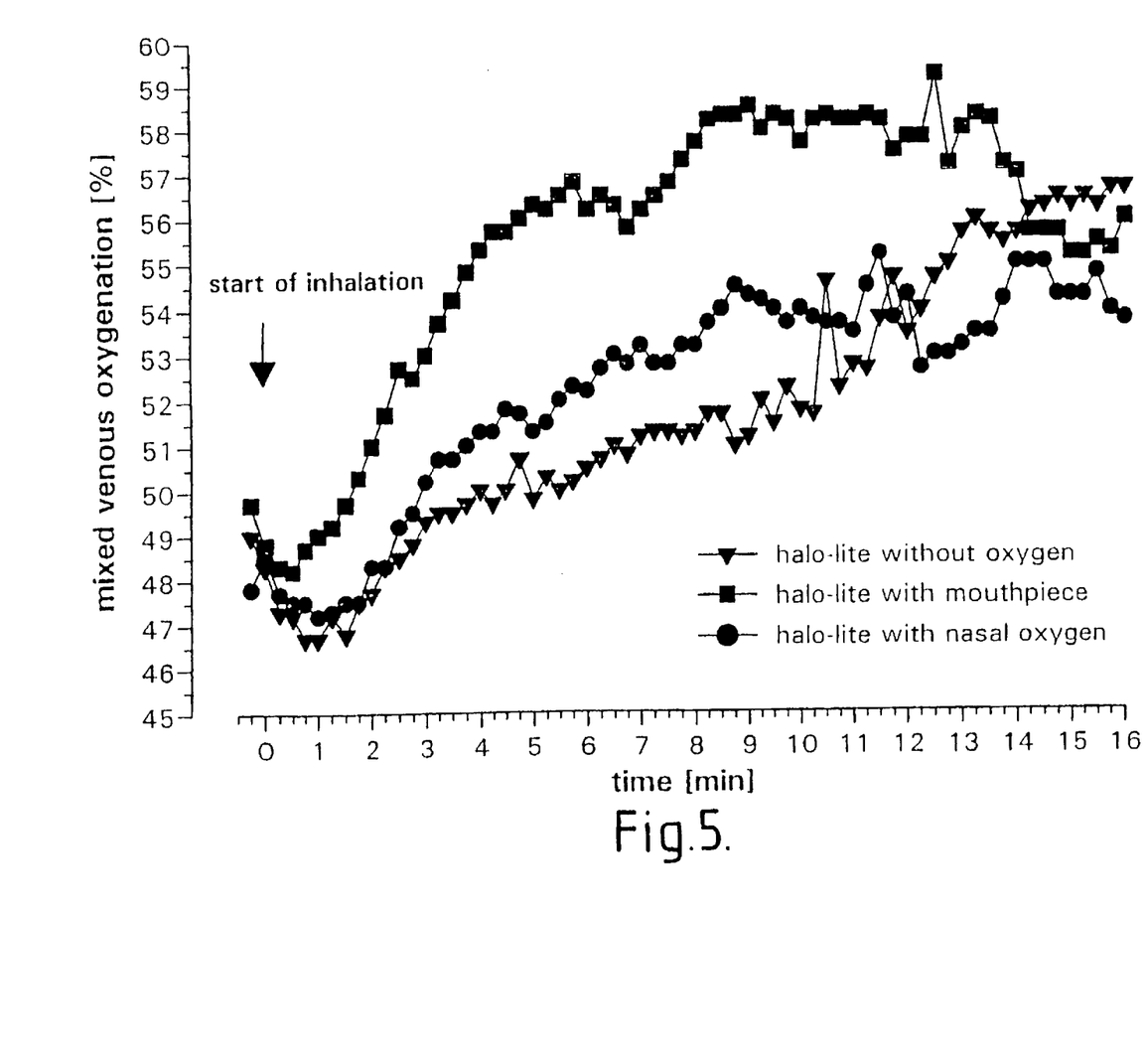
Figure 6:
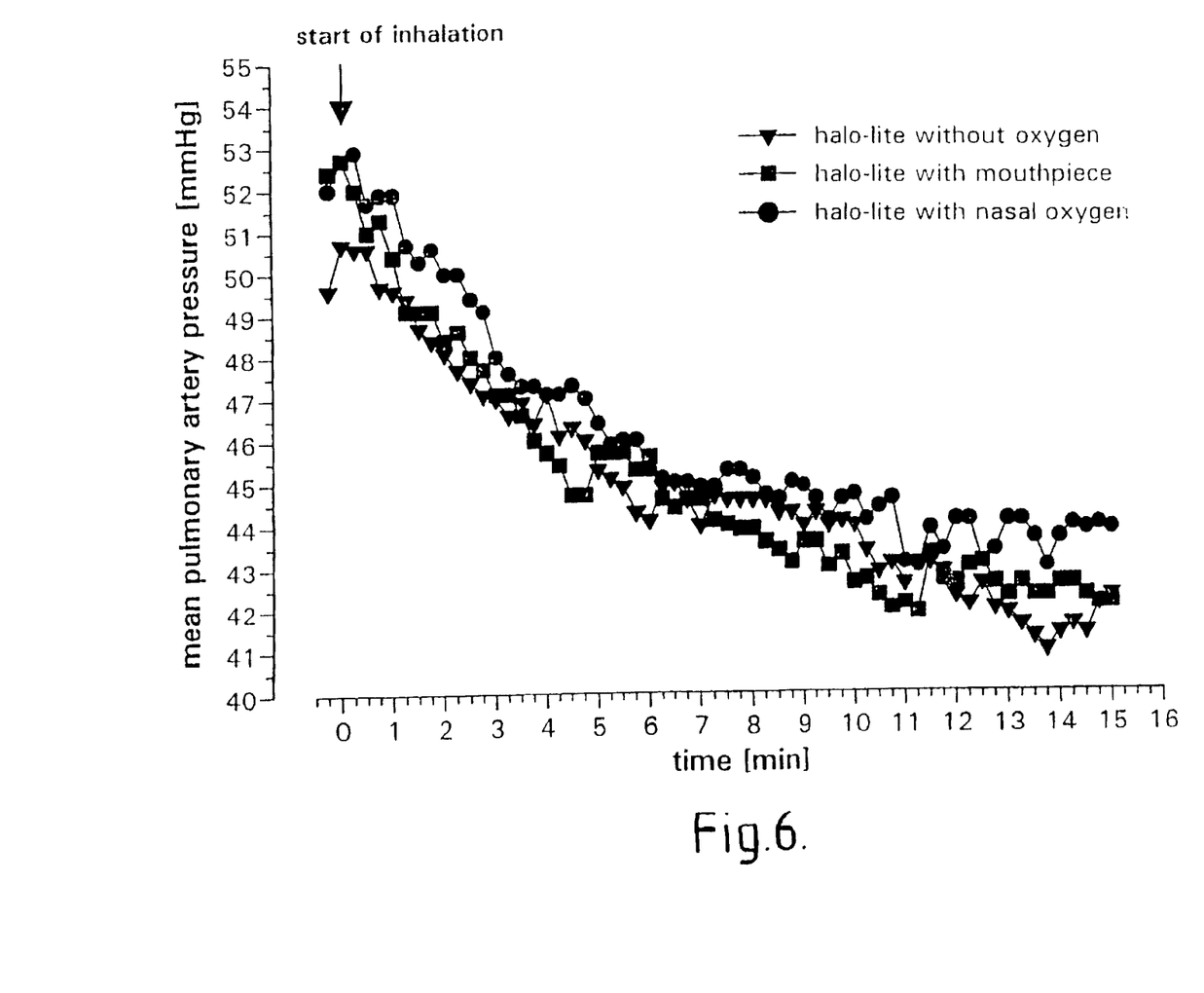

The results of the first test above are shown in FIGS. 1 to 6. FIGS. 1 to 3 show the effects of the withdrawal of oxygen supply, and FIGS. 4 to 6 show the effects of changing from oxygen supply to a HaloLite either without oxygen, or together with the mouthpiece which is the subject of the present invention or with nasal oxygen. It will be appreciated from FIG. 6 that the reduction in mean pulmonary artery pressure drops as a result of the administration of the drug. Of course, it will be appreciated that other drugs can be delivered in this way if a patient is oxygen dependent. Other prostocyclin drugs besides Iloprost can be used in the same way for pulmonary hypertension patients.

What is claimed is:

1. A combination mouthpiece for inhalation therapy devices, the mouthpiece being arranged to supply both a stream of air carrying an aerosolized drug and oxygen, and having a body (1) defining an aerosol duct (2) through which, in use, a stream of air carrying an aerosolized drug is supplied to a patient during inspiration; an inlet hole (4) through the body for receiving in a releasable and secure manner an oxygen tube adapter (5); wherein at least one partition (6) within the body (1) defining at least one oxygen duct (3), the oxygen duct being in a form such, that it extends generally parallel with the aerosol duct (2) and has a flow cross-section sized in order to guide a suitably large oxygen stream from the oxygen tube adapter (5) through the inlet hole (4) to the patient.

2. The combination mouthpiece according to claim 1, wherein the partition (6) is connected securely to the body (1) upstream of the drilled hole (4) in the direction of aerosol flow during inspiration, and from there on it is in a form such that it tapers in a funnel shape and is later tubular, so that the oxygen duct (3) completely and extensively surrounds the aerosol duct (2) in the form of an annular gap, the partition (6) between the two ducts being connected to the wall of the body (1), preferably in the region of the shortest connection between the hole (4) and the mouth-end opening of the mouthpiece, preferably by at least one connecting web (7) which extends in the direction of flow and which has a smaller width than the diameter of the hole (4).

3. The combination mouthpiece according to claim 1, wherein the partition between the aerosol duct and the oxygen duct is at least partly tubular whereby the oxygen duct surrounds the aerosol duct.

4. The combination mouthpiece according to claim 1, further comprising a connecting web arranged to join the body (1) and the partition (6).

5. The combination mouthpiece according to claim 1, wherein the partition tapers along at least part of its length.

6. The combination mouthpiece according to claim 1, wherein the at least one oxygen duct (3) defined by the at least one partition (6) extends in the direction of flow from the inlet hole (4) to the mouth-end opening of the body (1) and terminates flush with the latter.

7. The combination mouthpiece according to claim 1, wherein the partition (6) defining the oxygen duct (3) terminates in such a manner that it projects by a maximum of 1 cm beyond the mouth end opening of the body (1) in the direction of aerosol flow in the inspiration phase.

8. The combination mouthpiece according to claim 1, wherein that the partition (6) terminates at a distance of at least 1 cm beyond the mouth end opening of the body (1) in the direction of aerosol flow in the inspiration phase.

9. The combination mouthpiece according to claim 8, wherein the annular gap can be releasably closed in an airtight manner by an annular plug (8).

10. The combination mouthpiece according to claim 8, wherein that an annular flow screen (10) having an extensively varying width is provided in the oxygen duct (3), which is in the form of an annular gap, between the inlet hole (4) and the mouth end of the partition (6), so that the oxygen flow is rendered laminar by a suitable choice of the ring width of the flow screen (10), the width of the annular gap and the length of the partition (6), and the oxygen flow outside the oxygen duct (3), now guided only by the wall of the body (1) in the form of an annular flow, guides the inner aerosol stream at the same flow rate as far as the mouth end of the body (1).

11. The combination mouthpiece according to claim 10, wherein the longitudinal axis of the oxygen tube adapter (5) is inclined at an angle (a)<90° relative to the longitudinal axis of the basic body (1), preferably at a supplementary angle of 180° on the mouth side of the oxygen tube adapter.

12. The combination mouthpiece according to claim 10, wherein that an annular bead (9), produced from the same material as the body (1), is provided on the wall of the body (1), at a maximum distance of 1 cm from the mouth end opening of the mouthpiece.

13. The combination mouthpiece according to claim 12, wherein the partition and the part of the body which together define the aerosol duct are one piece and the remainder of the body is another piece.

14. A combination mouthpiece according to claim 13, wherein the piece which defines the oxygen duct is a sleeve.

15. A retrofit kit (N) for the retro-attachment of an oxygen duct (3) to a tapering tubular body (1) of a mouthpiece for inhalation therapy devices, the mouthpiece including an aerosol duct through which an aerosol stream is supplied to a patient during inspiration, having an inlet hole (4), wherein the retrofit kit (N) comprises:

- a tubular hollow body (N1) of relatively large diameter which is arranged to be attached to the body (1) of the mouthpiece to form an annular gap therebetween, and which has at least one inlet hole (N4), which can be closed in an airtight manner,
- an oxygen tube adapter (N5) which is connected to the hollow body (N1) at the site of the inlet hole (N4), the inlet hole being arranged to receive the adapter in a releasably securable manner,
- a funnel-shaped ring (N6) which is connected to the adapted hollow body (N1) at the end remote from the mouth.

16. A retrofit kit (N) according to claim 15, wherein the opening angle β and the width (B) of the preferably funnel-shaped ring (N6) are adapted to the taper angle β or to the tapering portion (S) of the body (1) in such a manner that the retrofit kit is in a form such that it can be slipped over the body (1), with a spacing of at least one mm therefrom.

17. A retrofit kit (N) according to claim 15, wherein an annular bead (N9) is fitted to the outside of the tubular hollow body (N1), and in that the funnel-shaped ring (N6) is in a form such that it can be secured firmly to the body (1), especially by adhesive bonding.

* * * * *

UNITED STATES PATENT AND TRADEMARK OFFICE
CERTIFICATE OF CORRECTION

PATENT NO. : 6,779,521 B1
DATED : August 24, 2004
INVENTOR(S) : Schmehl et al.

It is certified that error appears in the above-identified patent and that said Letters Patent is hereby corrected as shown below:

<u>Title page,</u>
Item [73], Assignee, should read -- Profile Drug Delivery Limited. --

Signed and Sealed this

Twelfth Day of October, 2004

JON W. DUDAS
*Director of the United States Patent and Trademark Office*